United States Patent [19]

Young

[11] Patent Number: 5,141,305
[45] Date of Patent: Aug. 25, 1992

[54] METHOD AND APPARATUS FOR EVALUATION OF PHASIC VISUAL NEURONS IN HUMANS

[75] Inventor: Rockefeller S. L. Young, Lubbock, Tex.

[73] Assignee: Texas Tech University Health Sciences Center, Lubbock, Tex.

[21] Appl. No.: 648,729

[22] Filed: Jan. 31, 1991

[51] Int. Cl.⁵ .......................... A61B 3/02; A61B 3/14; A61B 3/10

[52] U.S. Cl. .................................. 351/243; 351/210; 351/221

[58] Field of Search ............... 351/209, 210, 221, 243, 351/206, 207, 208; 128/664, 745

[56] References Cited

U.S. PATENT DOCUMENTS 3,533,683 10/1970 Stark et al. .
3,777,738 12/1973 Sugita et al. .
4,850,691 7/1989 Gardner et al. .
4,953,968 9/1990 Sherwin et al. .

*Primary Examiner*—Rodney B. Bovernick
*Attorney, Agent, or Firm*—Cox & Smith, Inc.

[57] ABSTRACT

An apparatus and method for evaluating substantially pure phasic-type neutronal activity associated with a specific pattern of pupil diameter variation comprises means for repeatedly measuring pupil diameter and for outputting signals representing the measurements; and means operatively connected to the pupil diameter measuring means for evaluating a pattern of pupil diameter variation in response to the presentation to a subject's eye of at least two images capable of eliciting a substantially pure phasic-type neuronal response.

8 Claims, 12 Drawing Sheets

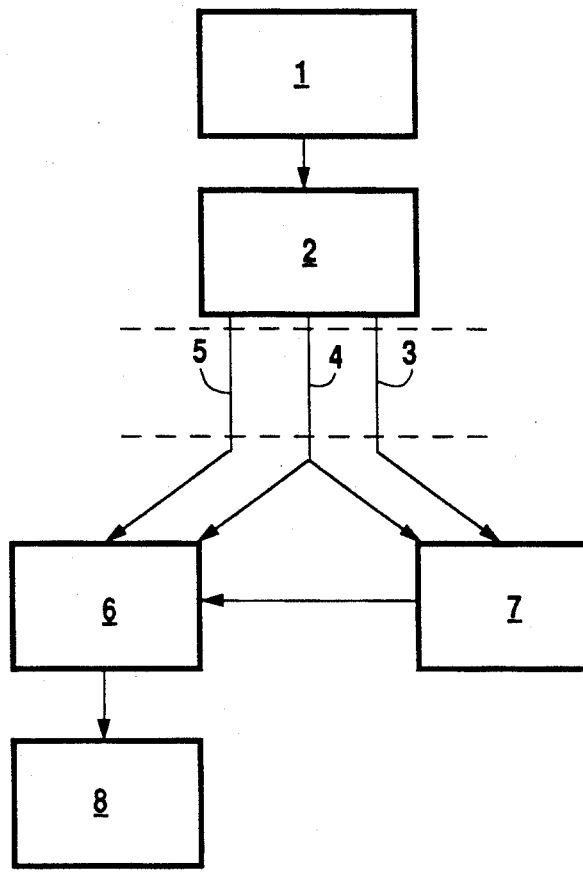
Fig. 1
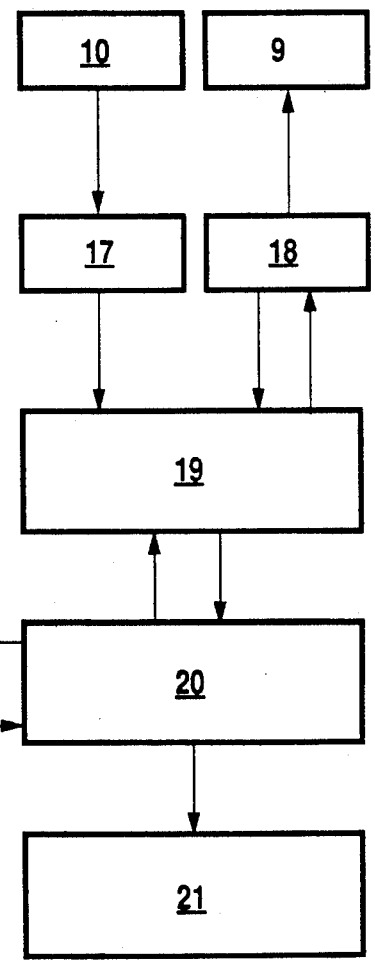
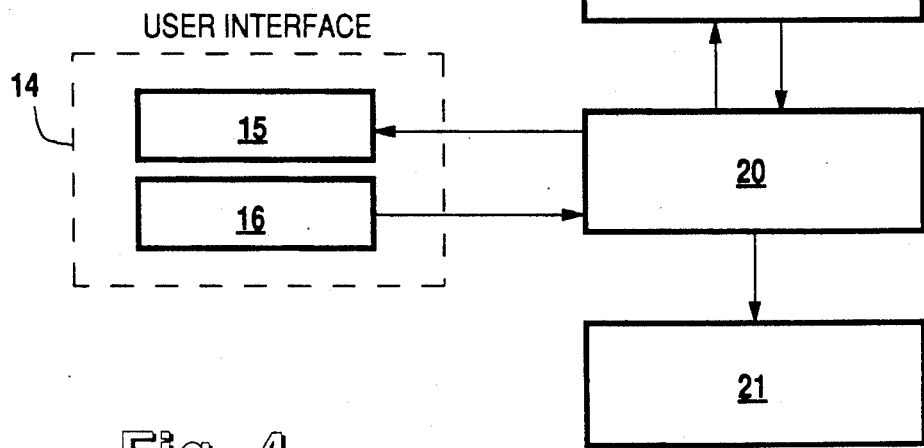
Fig. 4

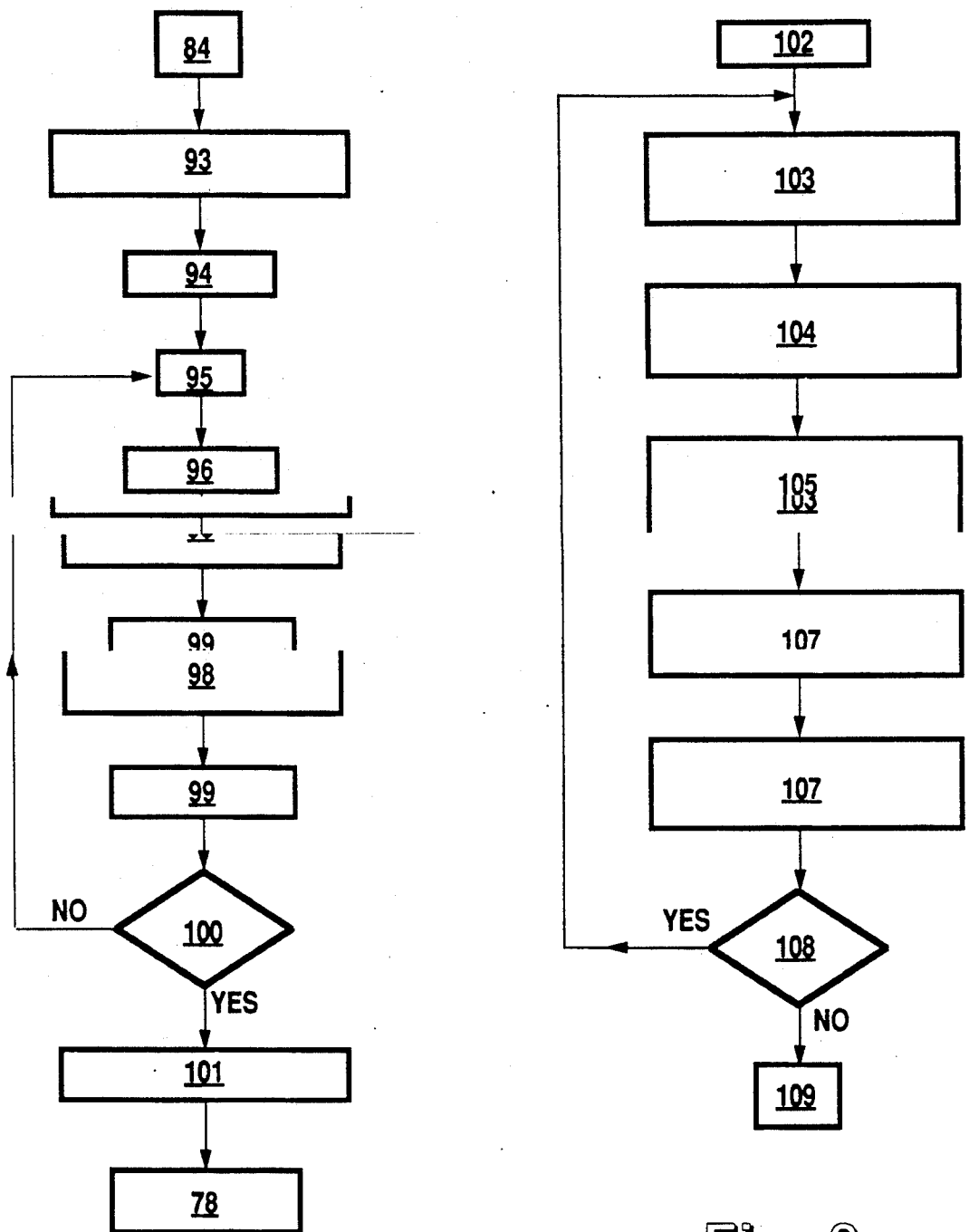

METHOD AND APPARATUS FOR EVALUATION OF PHASIC VISUAL NEURONS IN HUMANS

BACKGROUND OF THE INVENTION

1. Field of Invention

The present invention relates to a new method and an apparatus that is intended to be used in the medical and scientific fields concerned with vision, the eye, and perception. The invention provides a method for recovering information about phasic visual neurons, e.g., in humans. This information has importance in the diagnosis of pathologies of the visual system and in basic research concerned with understanding visual processing.

2. Description of the Background

Visual information received by the human eye is processed in the eye and then transmitted to the brain via about 1 million optic nerve fibers. In general, two broad classes of the optic nerves can be distinguished, those that respond phasically and those that respond tonically. The phasic fibers exhibit a burst of activity whenever there is a change in the color, luminance, etc., in the visual stimulus provided to the human eye. Otherwise, these fibers do not exhibit much activity. The tonic fibers are characterized by a continuous activity, that lasts as long as a stimulus is present. So, if the eye is looking at a red field which suddenly changes to green, many phasic fibers will exhibit a burst of activity in response to the change from red to green. After a change in color has occurred, however, the phasic fibers will remain silent once again. Some tonic fibers also respond to a change in color from red to green. The responses of tonic fibers, however, further differ from those of phasic fibers in that the tonic fibers maintain their activity for as long as the color green is present.

A recognized method for recording the activity of phasic optic nerves and the corresponding neurons they connect to in the visual system is by a microelectrode recording procedure. This method is the conventional technique used for recording the electrical activities of single neurons. Since this technique is invasive, however, it is not used routinely for the evaluation of the visual system in human subjects.

There are several non-invasive techniques currently being used that can provide some information about optic nerve function. One general technique is referred to as a "psychophysical" technique because it relies on an observer's visual perception and requires a voluntary, often verbal, response. The use of the psychophysical technique, however, is often limited, e.g., if the patient is not able to provide a voluntary response or if the patient's voluntary response is not reliable.

Another general technique is the one referred to as "Visual Evoked Cortical Potentials" (VECP). This technique relies on the recording of visually evoked "brain waves" that are measured by placing contact electrodes on the scalp of a subject. The electrical waveform of the responses measured is often complex and, therefore, difficult to interpret.

A third technique is referred to as the pattern-electroretinogram technique. This technique measures electrical signals within the eye believed to originate from nerve cells whose axons form the optic nerves of the eye. This technique, however, requires the placement of an electrode on the surface of the eye of the subject. The electrode does produce mild discomfort which can affect the patient's compliance with the test. In addition, the responses obtained are generally very small and therefore, hard to interpret.

U.S. Pat. No. 3,777,738 to Sugita et al. provides a method and apparatus for diagnosis using the pupillary light reflex to measure the response of the retina or optic nerves. This patent does not isolate the activity of phasic visual neurons, nor does it provide a method to evaluate functions of the phasic visual neurons such as color discrimination, spatial resolution, etc. The prior art patent does, however, provide a means for testing different areas of the patient's visual field, but the visual field assessment differs from that envisioned in the present patent. The prior art patent is concerned with the general loss of visual field capacity not with specific losses of phasic-type neuron function or with losses in color discrimination, spatial resolution, or other specific visual functions.

U.S. Pat. No. 4,953,968 to Sherwin et al. involves the assessment of evoked visual responses and provides a method to evaluate a number of visual functions including color sensitivity, contrast sensitivity, etc. The responses referred to in the prior art patent are, in contradistinction to the present technology, associated with visually evoked potentials that are EEG responses from the visual cortex of a subject. The prior art patent neither pertains to the evaluation of pupillary responses, nor to the use of pupillary responses to obtain information about visual function. Furthermore, the patent does not provide a method for isolating the activity of phasic visual neurons. The method of the prior art patent thus differs from the invention disclosed and claimed herein.

U.S. Pat. Nos. 3,533,683 to Stark and 4,850,691 to Gardner et al. relate to the measurement and recording of the pupillary diameter and latency of changes under various conditions. These prior patents are not concerned with the evaluation of visual function using the pupillary response.

Thus, the use of the pupillary light reflex to recover information about optic nerve function in humans has been known. Up to the present time, however, there does not exist a method for recovering information about a specific class of optic nerves, i.e., the phasic type, from the pupillary light reflex. The method using the pupillary light reflex described below affords numerous advantages over alternative approaches.

SUMMARY OF THE INVENTION

This invention relates to an apparatus for evaluating substantially pure phasic-type neuronal activity associated with a specific pattern of pupil diameter variation, that comprises means for repeatedly measuring pupil diameter and for outputting signals representing those measurements; and means operatively connected to the pupil diameter measuring means for evaluating a pattern of pupil diameter variation in response to the presentation to a subject's eye of at least two images capable of eliciting a substantially pure phasic-type neuronal response.

This invention also relates to a method of evaluating substantially pure phasic-type neuronal activity in a subject, which comprises (1) selecting values for $i_{max}$ of about 2 to 100, for $j_{max}$ of about 4 to 400 and for $k_{max}$ of about 3 to 200;
(2) blocking the sight of one eye of a subject;
(3) making $i=0$, $j=0$ and $k=0$;
(4) measuring a subject's pupil diameter;
(5) making $i=i+1$;

(6) making $k=k+1$;

(7) making $j=j+1$;

(8) providing to the fellow eye an image $I_i$ capable of effecting a substantially pure phasic-type neuronal response in the subject that is associated with a specific pupil diameter variation pattern upon a change in the image;

(9) measuring the pupil diameter $d_{ij}$ and calculating $v_{ijk} = d_{ijk} - d_{(i=0)jk}$;

(10) making $j=j+1$;

(11) repeating steps (7) to (10) every at least about 0.5 sec until $j=j_{max}$;

(12) repeating steps (6) to (10) every at least about 0.5 sec until $k=k_{max}$;

(13) repeating steps (5) to (12) until $i=i_{max}$;

(14) averaging all $v_{ijk}$, wherein $k=0$ to $k_{max}$ to obtain $v^{ave}_{ij}$;

(15) selecting the highest wherein $v^{ave}_{ij}$, wherein $j=0$ to $j_{max}$, to obtain $v^{ave}_{ih}$; and

(16) comparing each $v^{ave}_{ih}$ with $v^{ave}_{ih}$ (control) obtained by repeating steps (1) to (15) with at least one control subject lacking any phasic-type abnormal neuronal activity, wherein if the difference between $v^{ave}_{ih}$ and $v^{ave}_{ih}$ (control) is greater than or equal to a predetermined value the phasic-type neuronal activity of the subject is considered abnormal, and if it is equal to or less than the predetermined value it is considered normal.

A more complete appreciation of the invention and many of the attendant advantages thereof will be readily perceived as the same becomes better understood when considered in connection with the following drawings.

BRIEF DESCRIPTION OF THE DRAWINGS

FIG. 1 is a schematic diagram of the visual pathways mediating pupillary light reflexes.

FIG. 2 illustrates two types of pupillary responses.

FIG. 3 illustrates how the observer is situated during stimulation and recording of a pupillary response.

FIG. 4 is a schematic diagram of the stimulus and recording apparatus.

FIGS. 7a-7c flow charts of a response averaging program to perform off-line analysis.

FIG. 8 is a flow chart of a program to plot a hard copy of pupillary responses.

Figure 2A:
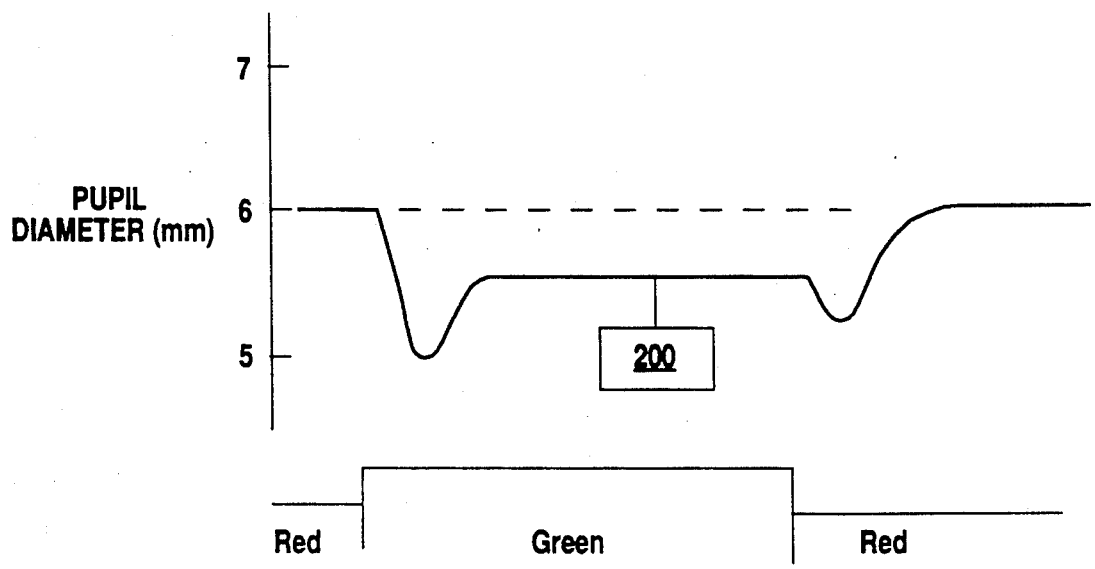
FIG. 2a depicts a response that has a tonic constriction component.

Other objects, advantages and features of the present invention will become apparent to those skilled in the art from the following discussion.

DESCRIPTION OF THE PREFERRED EMBODIMENTS IN REFERENCE TO THE DRAWINGS

The present invention provides a novel and unobvious method and apparatus for obtaining information about neuronal signals generated within the phasic (4) visual pathway in the eye (2) of a subject, including a human. The invention permits the evaluation of human subjects in a way that is non-invasive and does not require a voluntary, e.g., verbal, response.

One of the preferred uses of the invention is the detection of disorders that have specific effects on the "phasic-type" (4), i.e., the M-cell, magnocellular pathway, transient neurons, etc., visual neurons. Such disorders include glaucoma (Quigley, H. A. et al., "Chronic glaucoma selectively damages large optic nerve fibers", Investigative Opthalmology and Visual Science 28:913-920(1987)), and Alzheimer's disease (Sadun, A. A., and Bassi, C. J., "Optic nerve damage in Alzheimer's disease", Opthalmology 97:9-17(1990)), among others. The evaluation of phasic-type neurons provides a differential diagnosis to distinguish the above-mentioned from disorders such as optic neuritis that are believed to preferentially affect tonic-type nerves (3) while sparing for the most part phasic-type nerve function (King-Smith, P. E., et al., "Human vision without tonic ganglion cells?", in Color Vision Deficiencies II, Chapter 2, pp. 99-105, Adam Hilger Ltd. (1990); Wall M., "Loss of Pretinal ganglion cell function in resolved optic neuritis", Neurology 40:649-653(1990)).

The method of the invention is an indirect method comprising the recording of visually evoked pupillary responses (8) from which information about visual neurons, more particularly phasic neurons (4), may be inferred. The acquisition of information specific to the phasic (4) visual pathway is achieved by stimulating an observer's eye (2) with stimuli (1) designed to preferentially excite neurons within the phasic pathway (4) and produce a substantially pure phasic pupillary response (201).

The present invention also provides a system and an apparatus for stimulating the eye (2) of a patient with appropriate visual stimuli (1) and for acquiring, storing, and evaluating pupillary responses (8) from a patient.

This invention also provides a method for designing visual stimuli (1) that will produce pupillary responses (8) specifically and characteristically associated with the activity of phasic visual neurons (4) that yield clinically and/or physiologically relevant information about the neurons.

In addition, the invention discloses a hardware/software system configuration that provides a range of stimuli (1) and recording paradigms for testing visual parameters of a patient as defined above.

The present method utilizes the pupillary light reflex. This offers at least the following advantages over alternative approaches.

The response of a pupil to a stimulus (1) may be measured by remote imaging. The measurements may be made in the dark, through eye glasses and/or contact lenses and no electrodes are needed.

The pupillary light reflex does not require a voluntary, e.g., verbal, response from the subject.

The pupillary response (8) to light has a characteristic temporal wave form that is similar for most human subjects.

The response may be easily characterized, for example, by measuring its amplitude and latency.

This invention thus provides an apparatus for evaluating substantially pure phasic-type neuronal activity associated with a specific pattern of pupil diameter variation, that comprises means for repeatedly measuring pupil diameter and for outputting signals representing those measurements; and means operatively connected to the pupil diameter measuring means for evaluating a pattern of pupil diameter variation in response to the presentation to a subject's eye of at least two images capable of eliciting a substantially pure phasic-type neuronal response.

In a particularly preferred embodiment of the invention, the pupil diameter measuring means comprises of pupillometer. And still more preferred is a pupillometer that comprises a pupil image transducer operatively coupled to an electronic scanner for scanning a subject's pupil, and computing means operatively connected to the scanner for determining pupil diameter. A still more preferred embodiment of the invention is that where the pupil image transducer comprises a video camera.

Still another preferred embodiment, of the invention is that wherein the means for evaluating the pattern of pupil diameter variation comprises a data processing system.

In another preferred embodiment, the apparatus of the invention further comprises a visual output means for electronically presenting images of substantially equal luminance to the subject's eye, the visual output means being operatively connected to the means for evaluating the pattern of pupil diameter variation.

The above preferred embodiments of the invented apparatus are enabled and exemplified hereinbelow.

Also provided herein is a method of evaluating substantially pure phasic-type neuronal activity in a subject, that comprises (1) selecting values for $i_{max}$ of about 2 to 100, for $j_{max}$ of about 4 to 400 and for $k_{max}$ of about 3 to 200'
(2) blocking the sight of a subject's eye;
(3) making $i=0$, $j=0$ and $k=o$;
(4) measuring a subject's pupil diameter;
(5) making $i=i+1$;
(6) making $k=k+1$;
(7) making $j=j+1$;
(8) providing to the fellow eye an image $I_i$ capable of effecting a substantially pure phasic-type neuronal response in the subject that is associated with a specific pupil diameter variation pattern upon a change in the image;
(9) measuring the pupil diameter $d_{ij}$ and calculating $v_{ijk} = d_{ijk} - d_{(i-o)jk}$;
(10) making $j=j+1$;
(11) repeating steps (7) to (10) every at least about 0.5 sec until $j=j_{max}$;
(12) repeating steps (6) to (10) every at least about 0.5 sec until $k=k_{max}$;
(13) repeating steps (5) to (12) until $i=i_{max}$;
(14) averaging all $v_{ijk}$, wherein $k=o$ to $k_{max}$ to obtain $v^{ave}_{ij}$;
(15) selecting the highest $v^{ave}_{ij}$, wherein $j=0$ to $j_{max}$, to obtain $v^{ave}_{ih}$; and
(16) comparing each $v^{ave}_{ih}$ with $v^{ave}_{ih}$ (control) obtained by repeating steps (1) to (15) with at least one control subject lacking any phasic-type abnormal neuronal activity, wherein if the difference between $v^{ave}_{ih}$ and $v^{ave}_{ih}$ (control) is greater than or equal to a predetermined value the phasic-type neuronal activity of the subject is considered abnormal, and if it is equal to or less than the predetermined value it is considered normal.

In a particular preferred embodiment of this invention, the predetermined value utilized in step (11) of the method of the invention is about 2 standard deviations of the $v^{ave}_h$ (control) value. However, other predetermined values may be utilized as seen fit by the pratitioner.

The matter in which each and every step of this method may be practiced is described hereinbelow as are the parameters associated thereto. Any variations not described herein but which would be considered by an artisan to fall within the confines of this invention are also contemplated herein.

RECOVERY AND ISOLATION OF INFORMATION ABOUT PHASIC VISUAL NEURONS

Figure 2B:
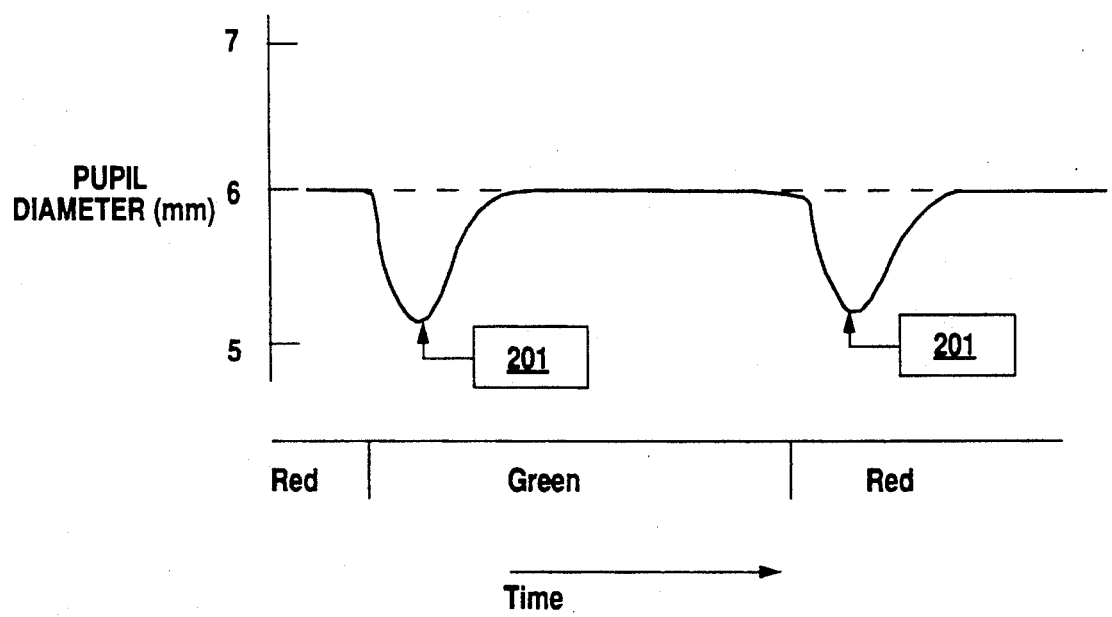
FIG. 2b depicts a response that consists of purely phasic constrictions.

How information about the phasic visual neurons may be recovered in human subjects will perhaps be better understood in reference to FIGS. 1 and 2 accompanying this patent. When presented to a human eye, a stimulus (1) will result in the excitation of different classes of optic nerves (3, 4, 5) that project to different locations in the brain. Phasic (4) as well as other types of optic nerves (3,5) project to the pretectal region of the brain and are primarily responsible for the pupillary light reflex. In addition, phasic-type optic nerves (4) project to other brain structures, which in turn project to the visual cortex (7). Nerves from the visual cortex (7) project back to the pretectum and are also involved in the control of pupillary diameter.

From the schematic diagram of the visual pathways shown in FIG. 1, it may be seen that the method of obtaining information about phasic-type optic nerves (4) of the invention comprises recording pupillary responses (8) to the stimuli (1). The pupillary response (8), in turn, can provide information about the activity of phasic-type visual neurons (4) either directly via the optic nerves or indirectly via the visual cortex (7).

The occurrence by itself of a visually evoked pupillary response (8), however, does not necessarily imply that the phasic optic nerves (4) have responded. The method of the invention ensures that solely pupillary responses (8) are produced by phasic-type optic nerves (4). The present method creates and/or utilizes visual stimuli (1) designed for this specific purpose.

The present method comprises identifying visual stimuli (1) that are known to generally evoke electrical responses (8) from phasic-type visual neurons (4) in primate species. This information is found in the research literature concerned with the neurophysiology of the visual pathway. (Robert Shapley, "Visual sensitivity and parallel retinocortical channels", in Annual Review of Psychology 41:635–58(1990)).

Electrophysiological results from primates are used, because at the present time no direct recordings of individual human neurons are available and the neurophysiology of the human visual pathway has been shown to be substantially similar to that of primates. An example of a stimulus (1) described in the literature is that of a rapid temporal exchange of color. Phasic visual neurons (4) respond vigorously when, e.g., a red spot of light is suddenly replaced by a green spot or vice versa. In general, all subtypes of phasic (4) visual neurons respond to a color exchange such as this one. The color change may involve other pairs of colors as well as other shapes in which the colors are presented.

Not all stimuli (1), however, necessarily result in a pupillary response (8), let alone one that is solely produced by phasic visual neuronal (4) activity. It is important to understand that each pupillomotor neuron (6) probably receives inputs from many visual neurons including non phasic-type (3,5) and different subtypes of phasic (4) neurons. The subtypes encompass phasic cells that have different stimulus-response phase relationships such as ON- and OFF- subtypes, different spatial summation properties such as linear and nonlinear subtypes, and the like. So, it is possible that the pupil might not respond to a stimulus that excites phasic neurons (4) if the signals from the individual phasic neurons cancel each other as they are summated within a pupillomotor neuron (6). Additionally, since not all visual neurons are of the phasic-type (4), non phasic-type (3,5) signals may also contribute to the pupillary response (8). Thus, the type of stimulus (1) utilized herein is to be selected as described.

The present method selects from among known stimuli (1), those that evoke a measureable and substantially pure phasic-type pupillary response (201) in a human observer's eye (2). Any stimulus (1) provided to the eye (2) of a patient must therefore lead to a measureable pupillary response (8). In addition, the stimulus (1) provided must also lead to a substantially pure phasic (201) pupillary response (8). Because phasic (4) visual activity produces a phasic pupillary response (201) whereas tonic (3) visual activity produces a tonic pupillary response (200), the requirement that the stimulus (1) also produce a phasic pupillary response (201) minimizes, if not eliminates, the possibility that the pupillary response (8) will be even partially mediated by tonic (3) nerve activity.

The pupillary response to each stimulus (1) of a human subject to a temporal exchange of, e.g., red for green spots and vice versa is then recorded in accordance with the present method. In general, all red-green exchanges will not produce a purely phasic pupillary response (201). Generally, a pupillary response (8) will also have somewhat of a "tonic" component (200), i.e., the pupillary diameter will either decrease or increase when compared to its baseline value (see, FIG. 2a). This increase or decrease persists over the duration of the red or green color presentation in a tonic response (200). A tonic component (200) is generally present when the stimulus provided has some attribute which causes a pupillary response (8) in non-phasic type (3,5) visual neurons. As such, these stimuli (1) are far from ideal and, are therefore, not suitable for use in the inventive method.

A purely phasic pupillary response (201) (see, FIG. 2b), however, may be produced when the red and green, or for that matter any two colors, presented to the eye (2) are of substantially similar luminance. The isoluminant red-green color exchange stimulus (1) is, among other isoluminant color pairs, suitable for use in the present method for the following reasons.

It is obtained in accordance with the method of the invention and is known to excite, at least, some subtypes of phasic visual neurons.

It produces a measureable and substantially pure phasic pupillary response (201).

The isoluminant red green exchange is, therefore, one example of many stimuli (1) selected as taught by the method of the invention.

In a further embodiment, the process of the invention also comprises further designing visual stimuli (1) used herein. The stimuli (1) suitable for use herein must not only evoke a phasic pupillary response (201) but may also be suitable for evaluating certain other clinically and physiologically relevant properties of phasic visual neurons (4). Such properties include, but are not limited to, spatial resolution, temporal resolution, contrast sensitivity, color discrimination, visual field sensitivity, and the like. These are all properties that are particularly well suited for testing phasic (4) neurons.

How the stimulus is designed in accordance with the method of the invention may be best understood in reference to a further example similar to that of the isoluminant color exchange stimulus (1) provided above. To be able to evaluate how phasic (4) neurons resolve spatial details, the isoluminant stimulus (1) may be modified so that it will have a spatial attribute. This spatial attribute may then be systematically varied and the pupillary response (8) to this variation detected. So, instead of an isoluminant homogeneous field that may be either red or green, or any other pair of colors, the stimulus may be modified to have a spatial pattern of vertical colored bars. The vertical bars may be colored, e.g., red and green, and be adjusted to be substantially isoluminant. To evoke a pupillary response (8) in the patient, images comprising the colored bars are exchanged. In this example, the red bars are substituted by green bars whereas the green bars are substituted by red bars. This version of the stimulus (1) retains the essence of the isoluminant color exchange, previously described for the full field color, while also being useful to measure an observer's pupillary response (8) as a function of, e.g., different bar widths. As, for instance, the width of the vertical bars is decreased, a point is reached beyond which the pupil no longer responds. The smallest bar width required to evoke a pupillary response (8) thus provides an estimate of the spatial resolution of phasic visual neurons (4) for that particular patient.

The isoluminant color exchange stimulus (1) may be modified to evaluate other clinically and physiologically relevant properties. The time course of the color exchange may also be varied to estimate the temporal resolution of phasic visual neurons (4). The colors used in the color exchange may be varied to estimate the neurons' ability to discriminate various colors. The location of the stimulus (1) may be varied to determine the sensitivity of the neurons in different parts of the visual field, and so forth.

POSITIONING THE OBSERVER FOR THE MEASUREMENTS

Figure 3A:
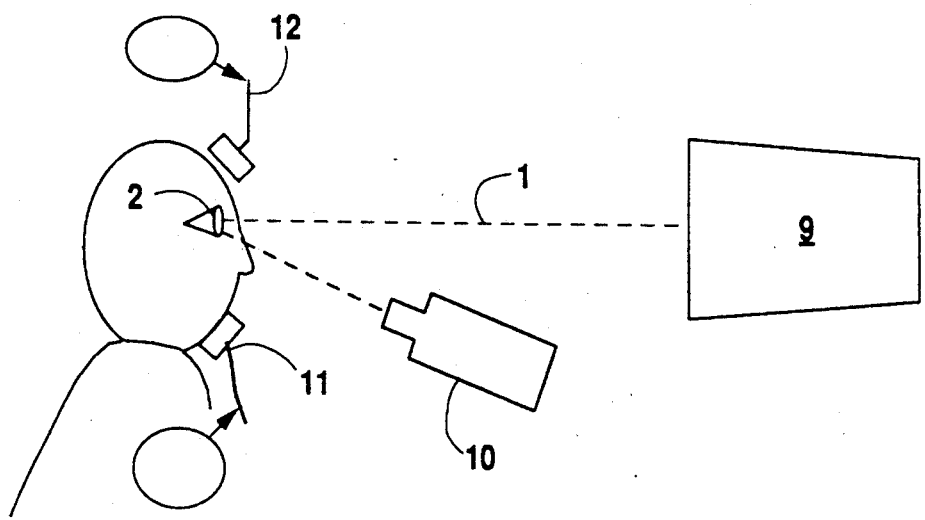
FIG. 3a illustrates a typical recording set up.

Referring to FIG. 3a, the observer may be seated with the head positioned on a chin rest (CR, 11) and/or forehead rest (FHR, 12). The visual stimulus (1) may be displayed, e.g., by means of flash cards, slides, pictures, or on a computer monitor (CM, 9). The center of the display, i.e., the CM (9) screen, is placed along the line of sight of a patient's eye (2) for testing. In this case, it is shown as the observer's right eye. A pupillary image transducer (PIT, 10) is placed in a location that minimizes the obstruction of the observer's eye (2) field of view, and yet provides adequate recording of the, e.g., right eye pupillary diameter. As shown in FIG. 3a, a typical location is below the line of sight of the same eye (2) being tested. The observer's left eye is patched when the right eye is being tested, and vice versa. To test the observer's left eye, the right eye (2) is patched and the forehead rest (12) and chin rest (11) may be laterally displaced so that the line of sight of the left eye is centered on the CM (9) screen or other stimuli (1)-providing medium.

Figure 3B:
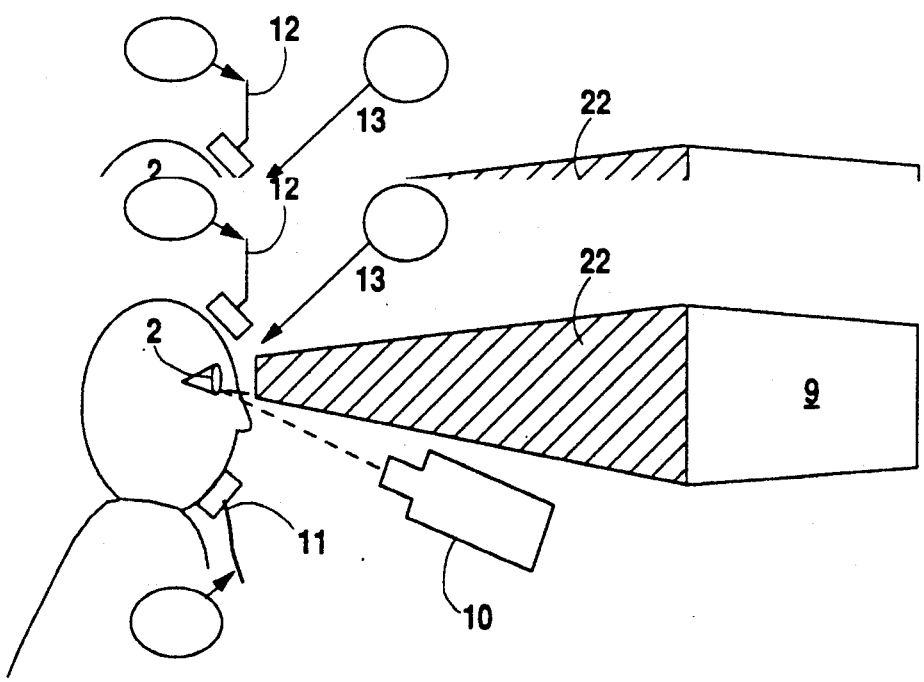
FIG. 3b illustrates how a typical arrangement can be modified to control for the effects of the pupillary response on the retinal image of a stimulus.
Figure 5A:
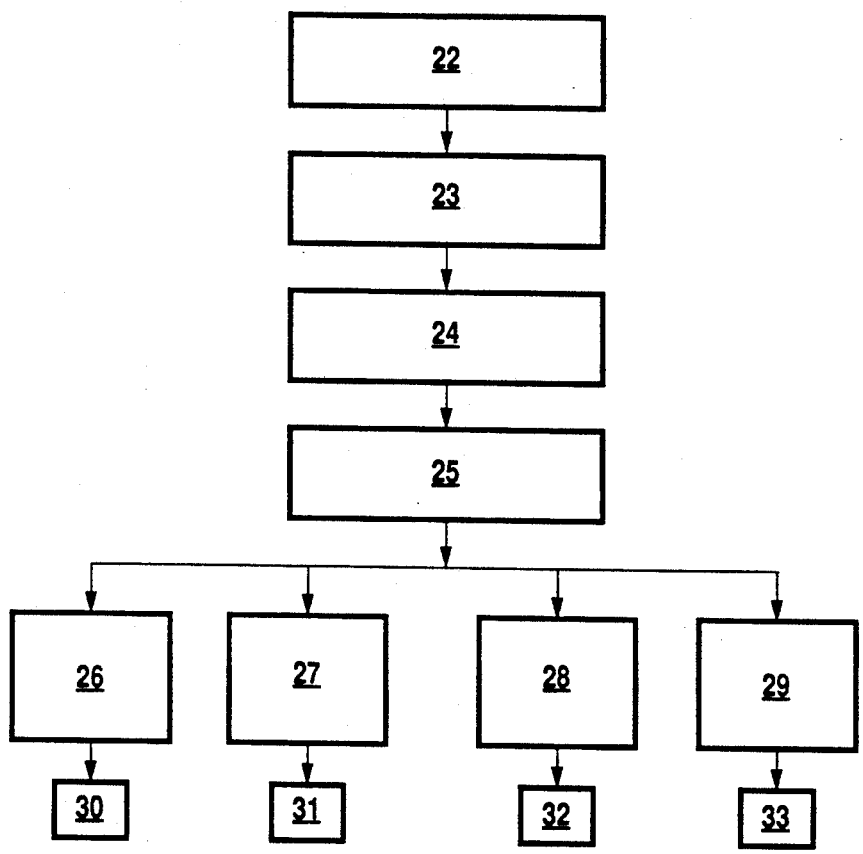
FIGS. 5a to 5e show one embodiment of the invention encompassing a flow chart of a response acquisition program that may be used on a "master computer", i.e., 80386.
Figure 5B:
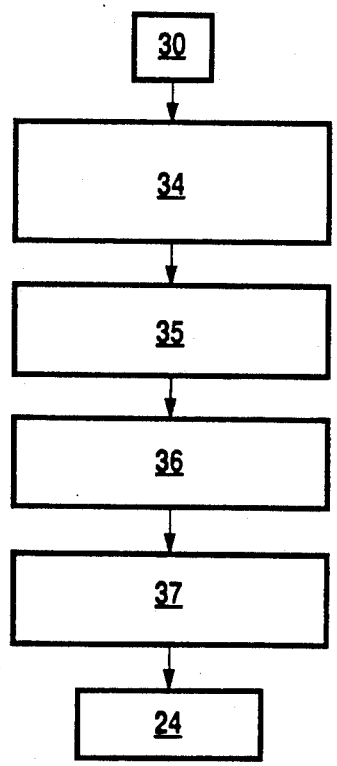
Figure 5C:
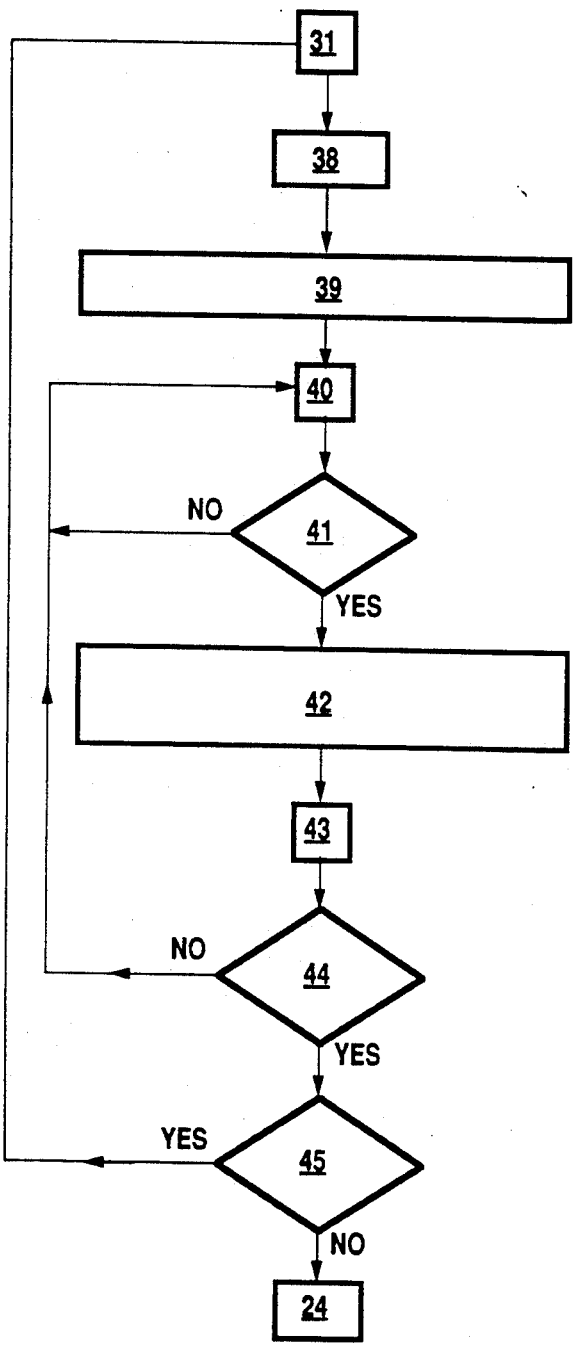
Figure 5E:
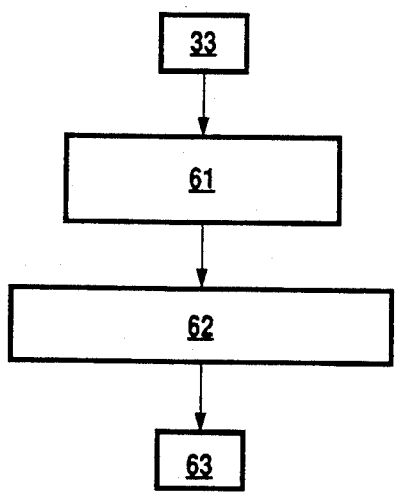
Figure 5D:
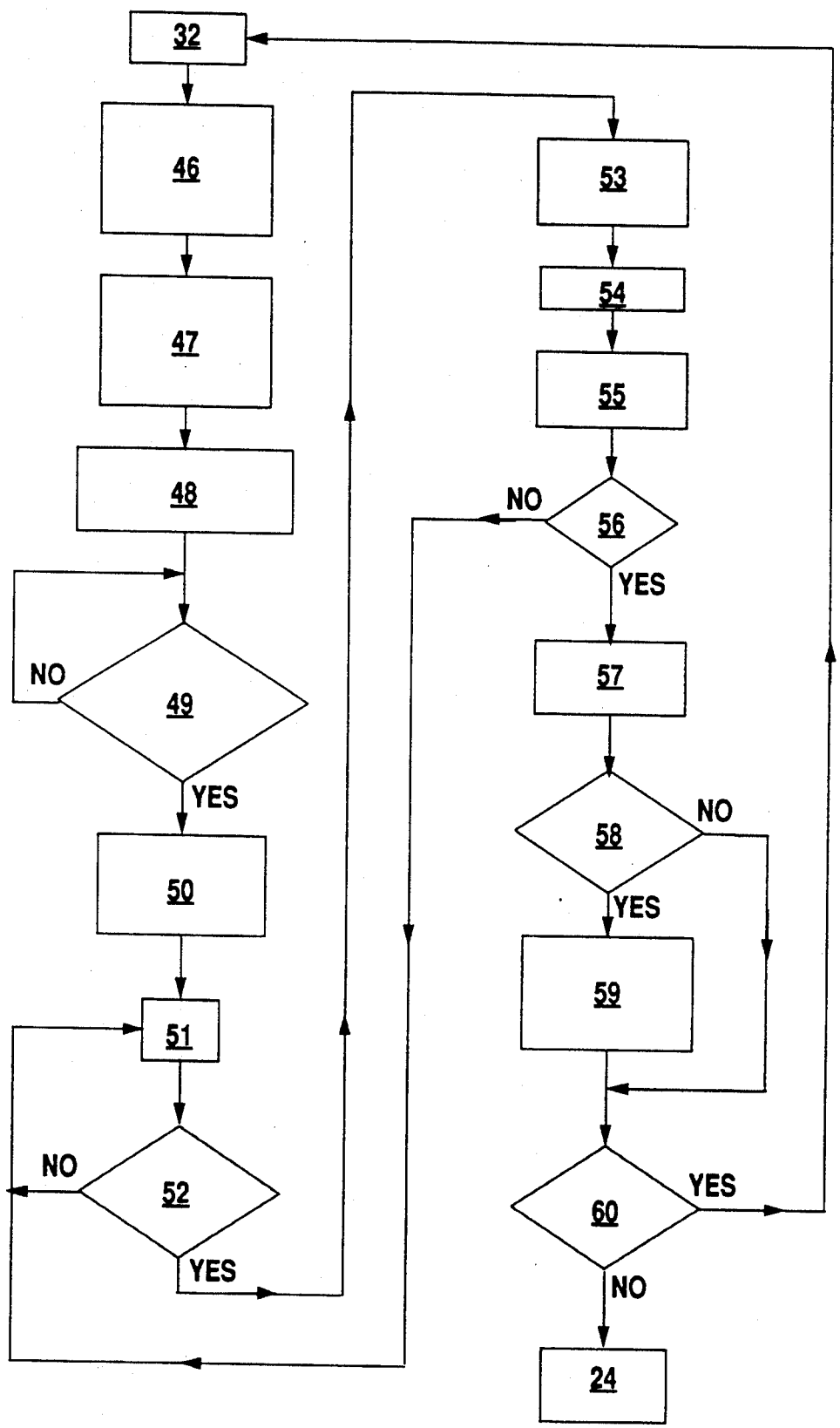

In a particularly preferred embodiment, the method is capable of controlling the generally small effects that pupillary responses (8) may have on the retinal image of a stimulus (1). To do so, an optical shield (OS, 22) may be placed in front of, e.g., the CM (9). The OS (22) functions in a manner similar to that of an eye (2) patch since it allows only one eye (2) to view the stimulus (1) whereas any vision of the other eye is being blocked. The OS (22) differs from an eye patch, however, in that it does occlude the vision of the one eye (2) while, at the same time, allowing the camera to view the pupil of the occluded eye (2). In FIG. 3B, the OS (22) is illustrated as having a pyramid-like shape. At the base, the OS (22) is rectangular and has a dimension similar to that of the CM (9) screen or other stimuli (1)-providing medium. In the figure, at the apex near the eye (2) of the observer, the OS (22) is narrowed to about 10 to 50 mm, and it preferably has an about 25 mm square aperture. A smaller aperture or artificial pupil (AP, 13) of about 1 to 4, and preferably about 3 mm diameter is placed at the apex. In FIG. 3B, the observer is shown looking at the display of a stimulus (1) through the AP (13) with the right eye (2). The AP (13) is generally smaller than the observer's natural pupil and thus, limits the aperture of the observer's right eye (2) that is being tested. The pupil's response (8) evoked by stimulating the, e.g., right eye, is measured from the pupil of the left eye, which responds consensually with the pupil of the right eye. The left eye will, however, remain unstimulated because the OS (22) obstructs its view. To record the responses (8) evoked by stimulating the left eye, the CR (11) and the FHR (12) are displaced laterally. Additionally, the PIT (10) is displaced laterally to record from the right eye (2) pupil.

FIG. 3 thus illustrates the general principles involved in the presentation of a stimulus (1) to the observer's eye (2) and the recording of the pupillary response (8). The figure is not intended to reflect the size or number of CMs (9) or PITs (10) nor the actual distances between them and the observer's eye (2).

In one preferred embodiment of the invention, the CM (9) covers the entire visual field of the observer's eye (2). The CM (9) consists, in this embodiment, of an array of CMs (9) spread across the entire visual field of the observer's eye (2). The PIT (10) is preferably small, e.g., as small as possible. The distance to the PIT(10) from the eye (2) affects the magnification of the pupillary image. The smaller this distance is, the greater the resolution of the pupillary diameter but the lesser the tolerance to small movements of the subject's head. Thus, a compromise must be reached so that a good, recordable and repeatable response is obtained with minimal interference from the observers movements.

A person with skill in the field would know how to position the various components with respect to the subject.

BASIC CONFIGURATION OF THE APPARATUS USED TO STIMULATE AND RECORD PUPILLARY RESPONSES

One embodiment of the system of the invention is shown in schematic form in FIG. 4. The apparatus shown in the figure is designed so that all of its functions may be placed under computer software control. However, in the simplest embodiment, all the operations may be conducted manually. The "master computer" comprises a general processor unit (GP, 20) shown in FIG. 4. The pupil response (8) data are input to the GP (20) via, e.g., a 9-bit data bus. This, however, may be conducted otherwise as is known in the art. The GP (20) communicates with a color graphics processor (CGP, 18), e.g., via another port. Visual stimuli (1) for display may also be generated by the CGP(18) software.

The system may be operated by a user or operator via, e.g., menu-driven software placed in the GP (20). A menu may be displayed on a video monitor (VM, 15) and the user's choices may be inputted, e.g., through a computer keyboard (KB, 16). In the method of the invention, a choice may be made by the user of either acquiring new pupillary responses (8) or analyzing old ones.

If the user selects acquiring new pupillary responses (8), the user may then further decide on one of the following.

The disk storage location for the response data.
The code-name of file used to store the data.
The particular visual stimulus to be tested.
When to start the stimulus-recording sequence.

If the user selects the analysis of old responses (8), the user may then further decide on one or more of the following.

To compute a mean value and 95% confidence limits of the response (8) waveform.
To obtain a hard copy of the response (8) waveform.
To measure the amplitude and/or latency of the response (8).

A hard copy of the response (8) may then be produced if desired by a hard copy device (HCD, 21), e.g., an x-y plotter. The amplitude and/or latency of the pupillary response (8) may then be displayed on the VM (15) and/or printed on the HCD (21).

The PIT (9) and CM (10) are shown at the top of FIG. 4. In one embodiment of the invention, the output of the PIT (9) may be processed by a pupillometer (PM, 17), a device that computes the pupillary diameter from the pupillary image at each moment in time. The processed pupillary diameter data may then be sent to the general processor (GP, 20) via, e.g., a data input/output interface (DIOI, 19). The user's stimulus (1) selection may then be sent from the GP (20) to the CGP (18) via the DIOI (19). Included among the information transferred to the CGP (18) may also be the user's choice of a stimulus (1), the pre-stimulus delay, the duration of the stimulus (1) presented, and the like. Upon receipt of a stimulus (1) choice, the CGP (18) may access from stored data all of the data needed for creating the selected stimulus (1). The data may then be loaded into the VM (15) of the CGP (18) so that the stimulus (1) may be displayed on the CM (9) instantly upon command from the GP (20). The information may also be transferred from the CGP (18) to the GP (20). In this case, the main information relates to whether the CGP (18) is ready to receive additional information and/or whether the CGP (18) is ready to display the stimulus (1).

When the user initiates a stimulus-recording sequence, the GP (20) begins reading the PM (17) output while simultaneously signalling to the CGP(18) to begin a stimulus (1) sequence. The stimulus (1) sequence may begin with a pre-specified delay period, i.e., the pre-stimulus delay that is followed by the initiation of a visual stimulus (1) for a prescribed period, i.e., stimulus duration. The recording period may be extended beyond the stimulus (1) offset. The purpose of the pre-stimulus delay is to acquire base line information (control) about the observer's eye (2) pupil diameter prior to stimulation. Typically, the delay period used is about 0 to 1 second, and most often about 500 msec. This period is not critical, but too long a period leads to inefficient data acquisition. However, when the method of the invention is operated manually, the delay period is in general longer. Too brief a period, on the other hand, may lead to an inadequate assessment of the pre-stimulation pupillary diameter because of the spontaneous fluctuations in the pupil diameter.

The duration of a stimulus (1) has importance in several situations. The duration of a stimulus (1) is important in the evaluation of whether the stimulus (1) produces a purely phasic pupillary response (201) or not. The stimulus duration, and the duration of the pupil response must be long enough to allow a pupillary response (8) to either return back to its baseline in the case of a purely phasic response (201) or to maintain an increased or decreased diameter in the case of a tonic response (200). The duration of the stimulus (1) is also of importance where the subject's pupil exhibits responses (2) at both the onset and offset transient of the stimulus (1), as illustrated in the examples shown in FIGS. 2a and 2b. The duration of the stimulus (1) must be long enough to avoid mixing these two responses (8).

The computer software may be made to display onto the VM (15), for instance, a temporal course of the pupillary diameter's change. Other information displayed may be the type of stimulus (1) used, subject's code, stimulus condition, and trial number. Different stimulus conditions may be numerically designated, e.g., by numbers 1 to 999. The trial number refers to the number of times a certain stimulus condition is repeatedly tested for one subject. In studies where the pupillary responses (8) to each stimulus conditions are expected to be very small, these may be recorded up to about 30 times (trials 1 to 30) or more. In many research situations, up to 100-200 trials or more may be appropriate if a lesser probability of error is desired. In a clinical environment, however, about 3-10 trials may suffice, and in some instances about 5 trials or less may suffice.

The system of this invention permits the display of a large number of different color/graphics stimuli (1). The data required to create different stimuli (1) may be computed beforehand and stored since the computations required for producing large numbers of stimuli (1) are time-consuming. The data may be stored, e.g., in a random access disk file in the CGP (18). When the user selects a stimulus (1), e.g., stimulus number 21, the CGP (18) will read only the data for that stimulus. Thus, the time required for the system to display a new stimulus (1) is brief, generally ranging from imperceptible or near zero to, at worst, about 10 seconds.

The present system permits the application or utilization of different stimulus' parameters including temporal modulation, spatial modulation, color, luminance, and the like. In one embodiment of the invention, this is accomplished by constructing stimuli (1) so that it is, e.g., software-generated. For example, the temporal modulation of a stimulus (1) is accomplished by animating each successive frame of the display with a slightly different stimulus (1). Spatial modulation may be accomplished by assigning a different color/luminance to each spatially different pixel or some other spatially defined unit (e.g., rectangles, circles, and the like) of a graphics display.

The present system permits the utilization of different stimulus-recording sequences by incorporating the control of the duration of the stimulus presentation and delays as well as the duration of the recording period into the computer software. The timing intervals may be attained by, e.g., creating a counter in the software. The counter may simply count a prescribed number of times and at its termination create a signal. The timing sequence may be incorporated into the GP (20) software and some aspects of the timing sequence then sent to the CGP (18) software.

One embodiment of the system of this invention permits the selection by the user of a different stimulus on each trial. In this embodiment, the user has the burden of keeping track of which stimuli have been tested at each point in time. In addition, the user is also charged with storing any response (8) obtained from one trial separately from that obtained from another. To store this information, the method may further comprise creating a filing system for responses obtained from different stimuli and different trials for each subject. The filing system may start with the creation of a file name incorporating, e.g., the subject's first and last name initial, a stimulus condition number, and a trial number. For example, the pupillary response (8) recorded for subject Rocky Young, for stimulus number 21 on trial number 45 may be designated as "RY02145". After a response is acquired, the computer may store the response under the assigned code, in this case "RY02145". The file name may then be placed in the disk drive directory of, e.g., a disk operating system (DOS), if one is available on the computer. Thereafter, when the user scans tests of patient Rocky Young with stimulus number 21, the computer scans the directory for "RY021" and determines the last trial completed, e.g., trial 45. After the subject's new pupillary response (8) is acquired, the computer program increments the trial number to 46 and then stores the new response as, e.g., "RY02146".

DESCRIPTION OF COMPUTER SOFTWARE

The software developed for the system and apparatus to practice one embodiment of the invention comprises several programs that are meant to be used during testing. The programs control stimulus display and response acquisition, among others. Other computerized programs are to be used after the responses have been acquired and are to be used to control the analysis of the response.

PROGRAMS AND FILES USED IN THE STIMULUS DISPLAY AND RESPONSE ACQUISITION (A) Response Acquisition Program The response acquisition program in fact comprises a group of computer programs. The programs, in general, accomplish various functions outlined below. However, different versions of these programs are possible to account for one or more of the following variables.

Differences in data format required to create certain visual stimuli.

Differences due to the capabilities, including input, output, and memory requirements, of the computer hardware.

Other variations due to the choice of computer hardware and other equipment.

A computer program designed for this purpose may have the following characteristics.

Allowing the user to input identification information on a subject, storing the information in the computer memory, and allocating computer memory for storage of the subject's responses.

Allowing the user to choose from various pre-defined stimuli (1).

Recording the subject's responses (8) to the selected stimulus (1).

Outputting from the GP (20) to the CGP (18) the information necessary to present the chosen stimulus (1) to the subject on the CM (9).

Allowing the user to trigger the start of a stimulus sequence, then begin inputting response data obtained by the PM (17) from the PIT (10), and outputting the pupil's responses (8) to the VM (15) or other output device. Optionally, it may produce an auditory tone or other signal to inform the user of the completion of a response period.

Allowing the user to reject or store the pupillary responses (8), and providing the user with an option to repeat the same stimulus (1) or select others.

A flow chart for one embodiment of the response acquisition program is illustrated in the flowcharts depicted in FIGS. 5-a to 5-e. As described in FIG. 5-a, the user may first enter information to identify a subject (22). Next, the program reads the stimulus menu file (23) in order to display the program menu (24) to the user. The program then obtains the user's menu choice (25) comprising one of four activities.

Selecting a stimulus condition (26).

Viewing the subject's resting pupil (27).

Stimulating and recording (28) any reaction(s) of the subject.

Exiting (29) the program.

If the user chooses to select a new stimulus condition (26), the program will then begin subroutine (30), an algorithm of which is illustrated in FIG. 5-b. The first step in the select-stimulus-condition procedure (30) is for the program to display a menu of stimulus conditions (26) to the user (34). Next, the user selects (35) from among the displayed conditions the stimulus condition that he/she wishes to display to the subject. The program then corroborates (36) the last trial number used for the selected stimulus, updates the trial counter by one (37), and then returns to the main menu (24) (See FIG. 5a).

A flow chart for a subroutine that views a resting pupil (31) is contained in FIG. 5-c. First, a time counter may be initialized to zero (38). Next the program may create messages to inform the user of the system status (39). The next step in the subroutine may be to decide whether the PM (17) is ready to return information regarding the subject's responses (41). If the PM (17) is not ready to return information, the program will wait (40), and, then again examine the status of the PM (41) once again. If the PM (17) is ready to transmit information, then the program will proceed to the display of information (42) regarding the subject's responses on the VM (15) in graphic form as a function of time. Next, the program will increment the time counter (43) and check to see if the response was recorded for at least a preset period of time (44). If not, then the program returns once more to examine (40) the status of the PM (17), and if so, the program may next ask if the user would like to repeat the same subroutine (45). If the response is affirmative, the subroutine (31) begins again. If the response is negative, the subroutine returns the user to the main menu (24).

FIG. 5-d sets forth a flow chart for a subroutine (32) to stimulate and record the elicited responses of a subject. The first step in this subroutine may send stimulus parameters (46) to the CGP (18) for display to the subject on the CM (9). Next, the subroutine may create a new record for storing results of the stimulus, and name the record according to the subject's initials, the stimulus condition number, and the trial number (47). The program may next display messages to the user of its status (48), and discern whether the user has instructed the program to begin (49) the stimulus (1). If not, the program waits and again asks if the user is ready, and if so, begins sending a signal to the CGP (18) to begin displaying (50) the stimulus (1) to the subject on the CM (9). The subroutine will next wait (51), and then ask whether the PM (17) is ready to send information (52) regarding the subject's response (8). If not, the program waits (51). If so, the program will store the data (53) regarding the subject's responses in a data array for future analysis, and increment the time counter (54). The subroutine may next display the data (55) obtained from the PM (17) as a function of time on the VM (15) for the user to observe the subject's responses (8). Next, the subroutine will check to see if the user has been monitoring the subject's responses (8) for at least the preset time period (56), and if not, will return to wait (51) for more information from the PM (17) and repeat steps (52) to (56). If the subject's responses have been monitored for at least the preset time period, then the program may signal with an auditory tone (57) the end of the time interval for the response period. Next, the subroutine may ask the user if he wants to store information (58) regarding the subject's responses (8) for future analysis. If so, the program may store the information in the memory using the record name after initializing it (59). If not, the program asks if the user wishes to repeat (60) the same stimulus (1). If the same stimulus is to be repeated, the subroutine will begin once again (32). If once the stimulus is not to be repeated, the subroutine returns to the main menu (24).

A flow chart for a subroutine to exit (33) the display response acquisition program is depicted in FIG. 5-e. The subroutine may begin by initializing the duration of a stimulus to zero (61), and then send the stimulus (1) parameters to the CGP (18) to display (62) on the CM (9). The program used in the stimulus display and response acquisition may end (63) at this point.

(B) Stimulus Display Program

The stimulus display program (76) comprises a group of computer programs to display stimuli (1) to a subject to be tested. Different programs may be written for creating different visual stimuli (1). The programs may vary and may be adapted to the specific characteristics of the equipment chosen. In one embodiment of the invention, the stimulus display program has the following capabilities.

Presenting a chosen stimulus (1) to the subject by transmitting parameters for the stimulus (1) from memory, e.g., in the GP (20), or from newly input information, to the CGP (18) to be output to the subject, e.g., on the CM (9).

Inputting information regarding the subject's pupillary response (8) measured by the PIT (10) to the PM (17), which in turn outputs information regarding the subject's responses (8) to the computer memory and/or to the user.

However, the latter may be omitted.

Figure 6:
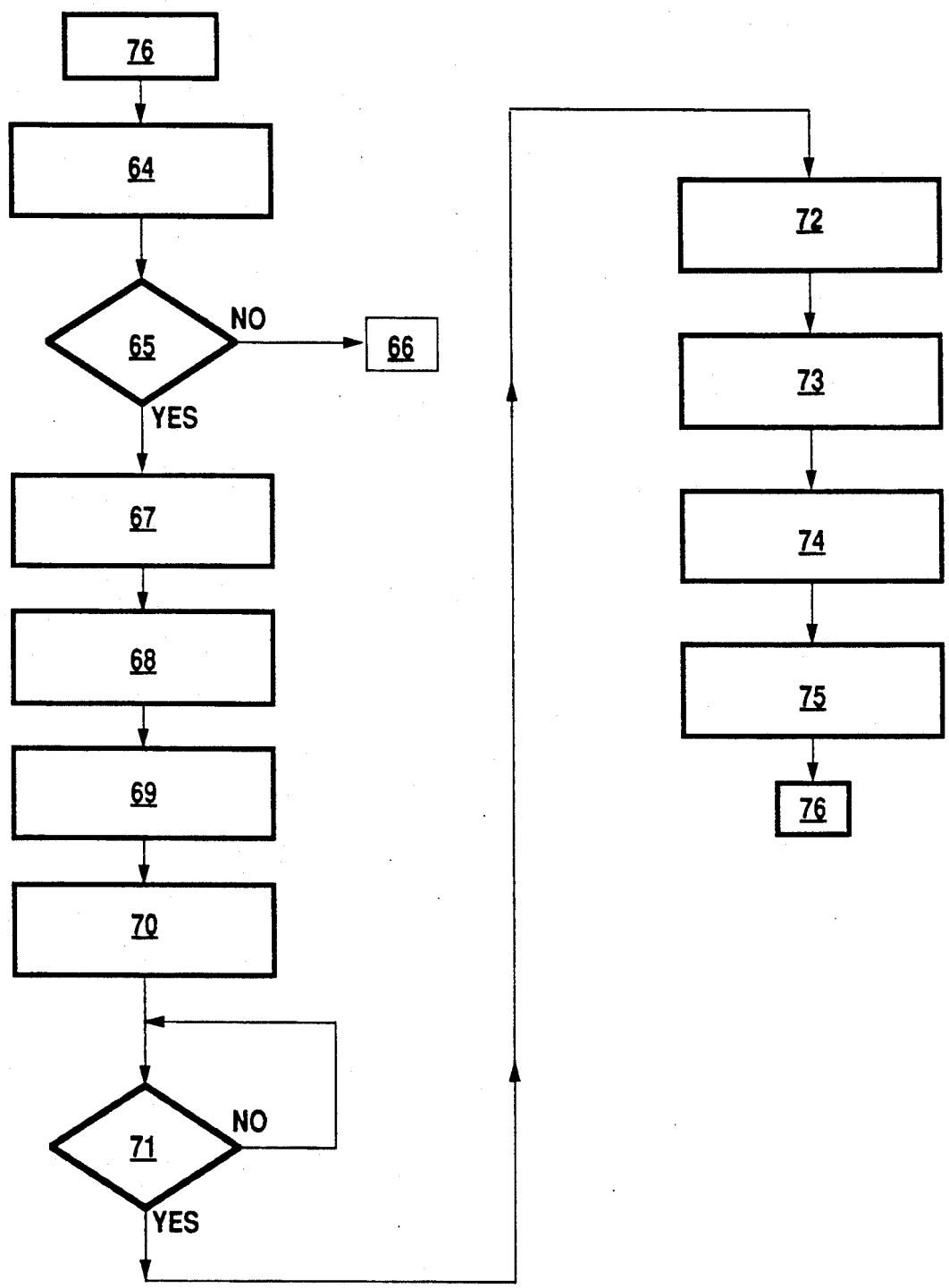
FIG. 6 is a flow chart of an embodiment of the invention encompassing a stimulus display program. This or another program may be used on a color-graphics processor, i.e., MAC II.

An algorithm for one embodiment of the stimulus display program (76) is depicted in FIG. 6. The stimulus display program (76) may begin by reading the stimulus parameters sent by the GP (20). The information for step 64 in this chart comes from step 46 in FIG. 5-d, where the acquisition program sends the stimulus parameters to the CGP (18). Next, the stimulus display program (76) will discern whether the time parameter for the stimulus' duration is greater than zero (65). If not, then the stimulus display program (76) will end (66) prematurely. If so, then the stimulus display program (76) next reads (67) the stimulus data file from CGP (18)'s memory, and loads it into video memory (68) in order to display the initial stimulus screen (69). Next, the display program may add fixation dots to the stimulus screen (70), and wait for a start (71) signal from the GP (20) to begin the stimulus (1). The input regarding this start signal comes from step 50 in the response acquisition program. (See FIG. 5d). If the signal does not come, the display program will wait. If the signal to start comes, then the display program will begin a pre-stimulus delay loop (72), animate the stimulus display (73), begin a stimulus duration delay loop (74), and restore the original stimulus screen (75) after the stimulus sequence is completed. The stimulus display program (76) may next return to the beginning of the display program (76) to await new stimulus parameters (76) from the GP (20).

(C) Stimulus Menu File

This is a list of information which delineates the choices a user may make amongst stimuli and/or experiments and the variables associated with them. This file may be enlarged or reduced by adding or subtracting experiments, variables in experiments, and stimuli, and will differ in format based upon the equipment selected for a particular embodiment of the invention. For example, in one embodiment of the file, the list may include the name of the equipment, the number of stimuli to be included in the user's menu, the pre-stimulus delay period, the stimulus duration, the condition number assigned to each stimulus, and a list of parameters associated with each stimulus (1).

(D) Stimulus Data File

This is a collection of data, e.g., a detail of the color/luminance settings, required to display various stimuli (1) listed in the stimulus menu to the subject, e.g., on the CM (9). Like the stimulus menu file, this file may be enlarged or reduced by the addition or subtraction of stimuli (1). In one embodiment of the stimulus data or menu file, the file may be organized so that the data associated with different stimulus condition numbers may be read from a disk using a random access read procedure.

PROGRAMS USED FOR OFF-LINE RESPONSE ANALYSIS (A) Response Averaging Program

This is a computer program used to analyze the responses obtained on individual trials of a subject. Different versions may be written to accommodate one or more of the following.

Differences in analysis techniques utilized,
Differences due to the capabilities of the equipment chosen, and
Differences due to format of output desired.

A computer program designed for this purpose may have the following characteristics.

Allowing the user to choose information to be analyzed, e.g., which subject and which stimuli.
Computing the mean base line pupil diameter, i.e., the diameter prior to the stimulus (1) onset, the mean change in pupil diameter relative to the base line, and a confidence interval around the main diameter change.
Performing other signal processing routines, e.g., filtering, to improve the signal to noise ratio of the response.
Outputting the results of the analysis to the user, e.g., in graphic form on the VM (15).

Figure 7B:
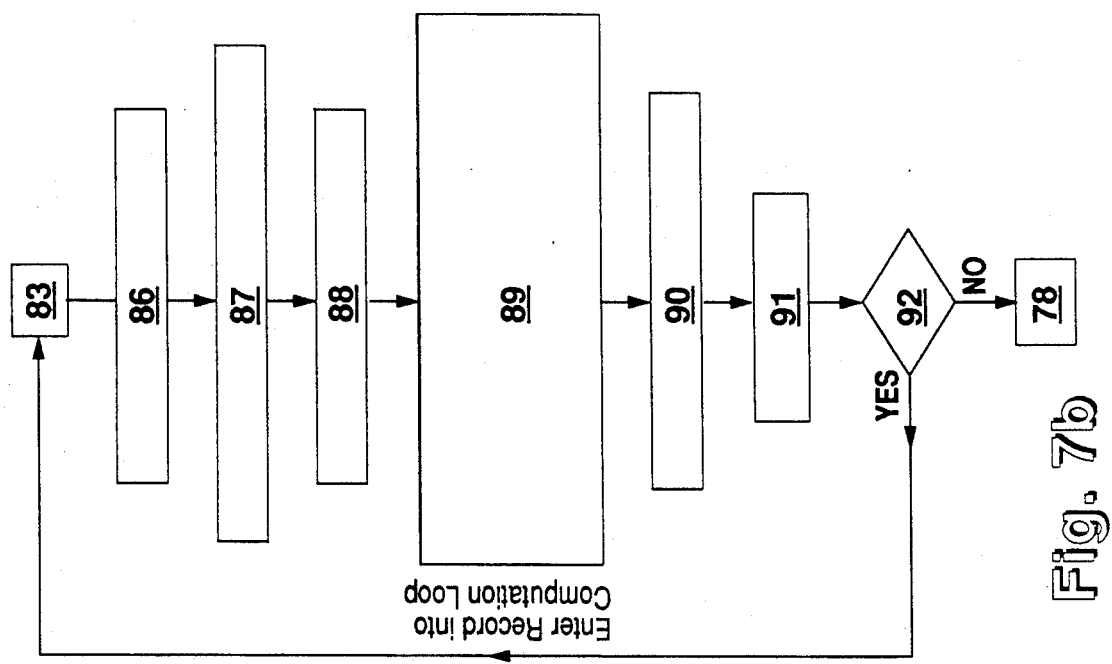
Figure 7A:
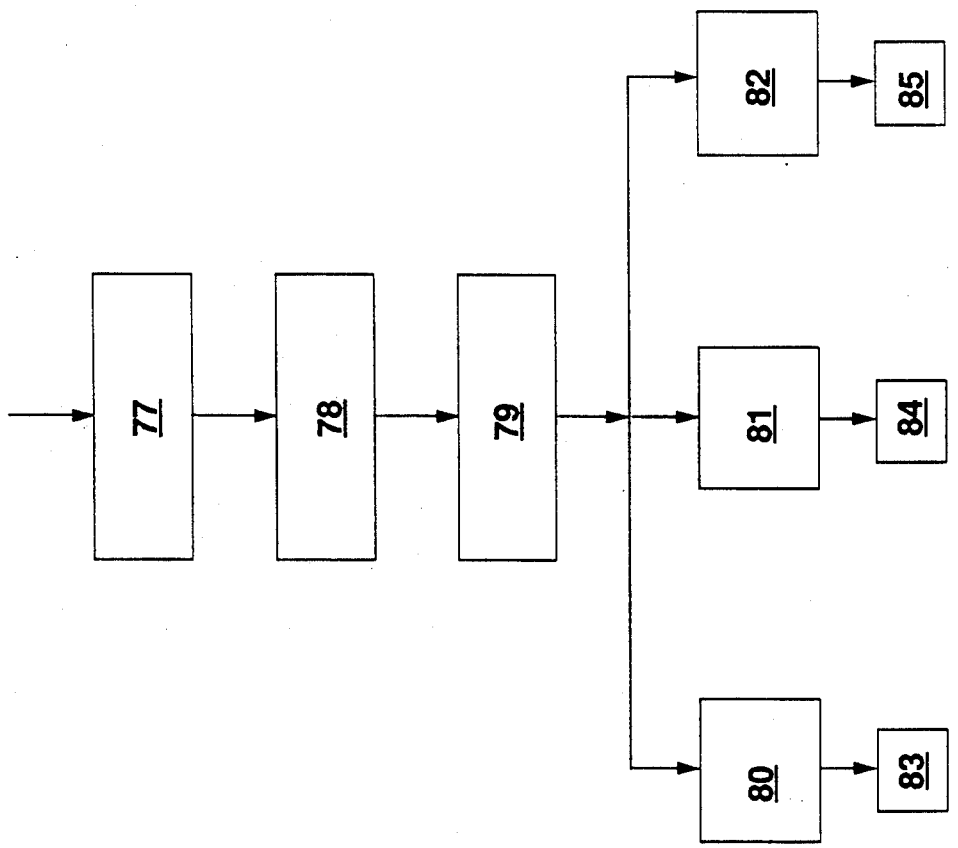

A flow chart for one embodiment of the invention is illustrated in FIGS. 7-a to 7-c.

As FIG. 7-a illustrates, this embodiment provides the user with two alternative methods for retrieving individual trials. The first step in the chart depicted in FIG. 7-a permits the user to choose which subject's responses (8) are to be analyzed (77). Next, the program displays a menu of choices (78) to the user regarding the function to be performed, and obtains the user's choice (78) thereto. This response may either be to preview an average (80), to average from a batch list (81), or to quit (82). If the user's choice is to quit (82), the program then terminates (85). If the user's choice is to preview an average (80), the program begins a preview and average subroutine (83) as depicted in FIG. 7-b. A choice by the user to average from a batch list will initiate a batch list subroutine (84), as depicted in FIG. 7-c.

The preview and average subroutine (83) may begin by asking (86) the user which stimulus condition number and/or trial number to analyze. Next, the subroutine may locate the record of the requested information (87), input that information, and display it to the user (88). Next, the subroutine may enter the information from the record into a computation loop (89), which performs the following calculations.

1. Baseline pupil diameter=average first ten data points.
2. Relative diameter(t)=Data(t)−Baseline.
3. Sum(t)=sum(t)+Relative diameter(t).
4. SumSquare(t)=SumSquare(t)+(Relative diameter(t))$^2$.

After these computations, the subroutine may compute a mean value and a standard error of the mean (90) and display the waveforms (91) to the user on the VM (15). The subroutine then determines whether the user wishes to preview the responses to another stimulus condition, and if so, all its steps (92) will be conducted again. If the subroutine is not to be repeated, it returns to the main menu (78).

A subroutine for analyzing an average from a batch list (84) is depicted in FIG. 7-c. The program begins by having the user enter the file name of a batch file (93). Next, a counter variable is initialized to 1 (94), and the GP (20) reads the batch file (96). Once the batch file information has been read (96), the subroutine may begin examining each record (97) and completing the computation loop (98) with the data from that record (98). The computation loop 98 in FIG. 7-c is substantially equivalent to the computation loop 89 in FIG. 7-b. After the computation, the program will increment the counter (99), and discern whether that counter has exceeded the total number of records read in the batch file (100). If not, the program returns to step 95 to examine the next record. If all of records have been examined, then the program displays the waveform (101) and exits to the main menu (78).

(B) Response Display Program

This is a computer program that may be used to obtain a hard copy of a subject's responses. The flowchart for one embodiment of this invention is illustrated in FIG. 8. In this program, the user first chooses which information to display (103), the program then reads the response from memory, displays this information to the user (104) and outputs it to the plotter (105). The program then obtains the amplitude and time calibrations from the user (106) and outputs them to the plotter (107), and it finally determines whether to repeat the program (108). If so, the program begins again (102), but if not, the program terminates (109).

(C) Response Measurement Program

Figure 9A:
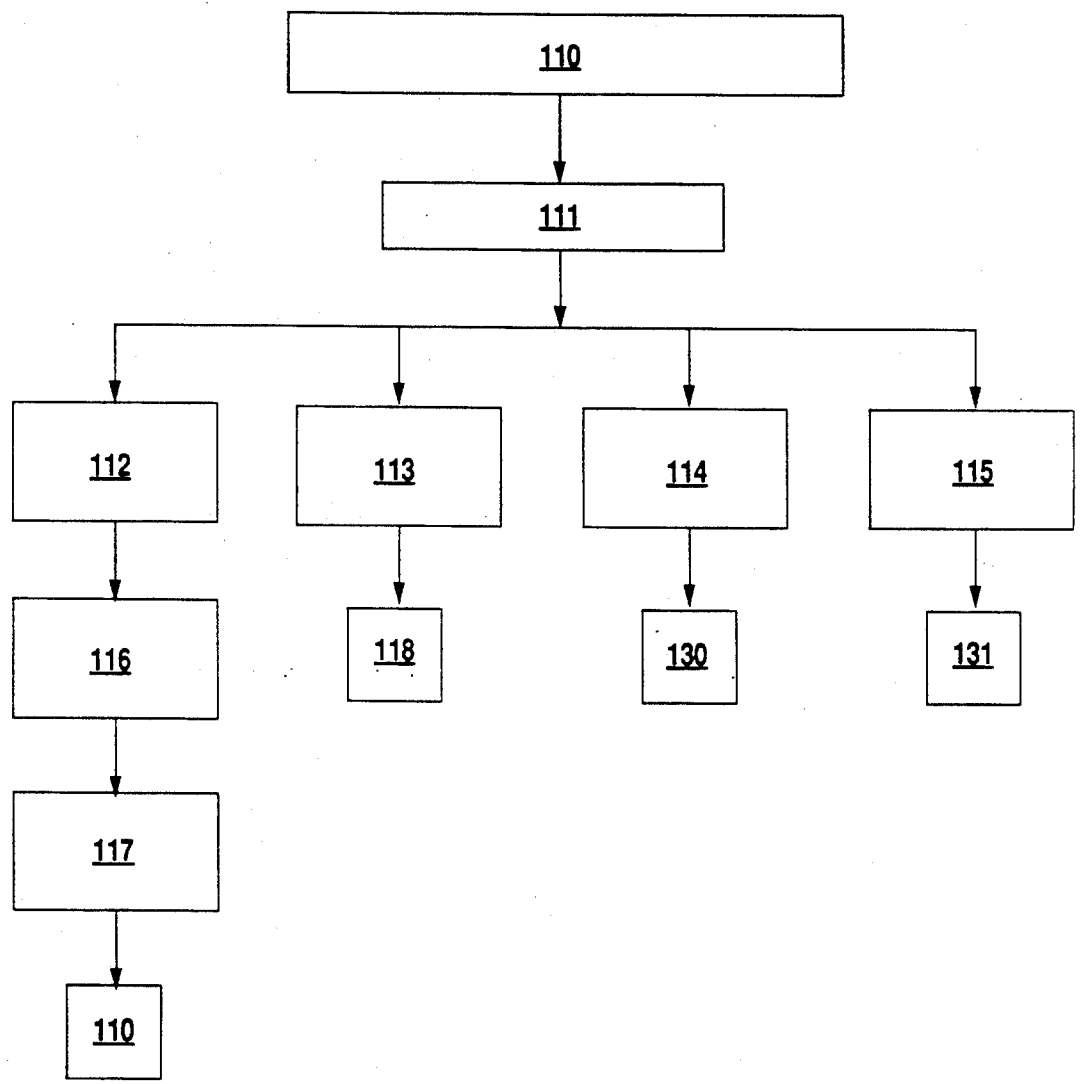
FIGS. 9a to 9c show one embodiment of the invention by means of a flow chart of a program that allows a user to measure the amplitude and latency of a pupillary response.

This is a computer program that allows the user to measure a subject's average responses (8) to stimuli (1) obtained from the response averaging program. The response measurement program reports to the user information on pupillary base line, i.e., the diameter in millimeters prior to onset of the stimulus (1), the amplitude of pupil constriction, i.e., the decrease in the diameter relative to the baseline diameter, and the latency of pupillary response (8) relative to the onset of the stimulus (1). FIGS. 9-a to 9-c are flowcharts representing one embodiment of the response measurement program, which allows the user to measure responses of a subject while acquiring information about the absolute pupil diameter (see, FIG. 9-b) or about the pupil diameter relative to the baseline (see, FIG. 9-c).

The first step in the response measurement program is to obtain from a menu (110) the user's choice (111), which may be either to enter a file name (112), to display responses with one cursor (113), to display responses with two cursors (114), or to quit (115). If the user's choice is to enter a file name (112), then the program (110) prompts the user to enter the subject and stimulus condition for which to measure a response (116), and then inputs that information from the memory (117). Then the program returns to the main menu (110). If the user's choice is to display information with one cursor, then the program begins the subroutine described in FIG. 9-b (118). A choice to display information with two cursors (114) begins the subroutine depicted in FIG. 9-c (130). Finally, if the user's choice is to quit the program (115), the program ends (131).

When the user chooses step (113), a subroutine to measure responses of a subject while acquiring information about the absolute pupil diameter begins (118). This subroutine is depicted in FIG. 9-b. This subroutine begins by displaying a response in waveform to the user (119). Then, by way of an interactive subroutine such as a "move cursor routine", the user may mark the location of a point on the response waveform that he wishes to measure. The user may then move the cursor by pressing the LEFT or RIGHT arrow keyss found on the keyboard.

The "move cursor routine" (124) displays the cursor on the waveform (121), and displays the amplitude and latency of the response waveform at the point designated by the cursor (122). In this routine, the program first discerns whether the user has input a left arrow (125). If so, the program tells the output device to move the cursor to the left (126), and returns to step (120) in the subroutine. If the user did not enter a left arrow, then the routine discerns whether the user entered a right arrow (127), and if so, instructs the output device to move the cursor to the right (128), and returns to step (120) in the subroutine. If neither a right or a left arrow is entered, the subroutine discerns whether the user desires to quit the program (129), and if not, returns to step (123) in the subroutine. If the user does decide to quit, the program returns to display the main menu (110).

Figure 9B:
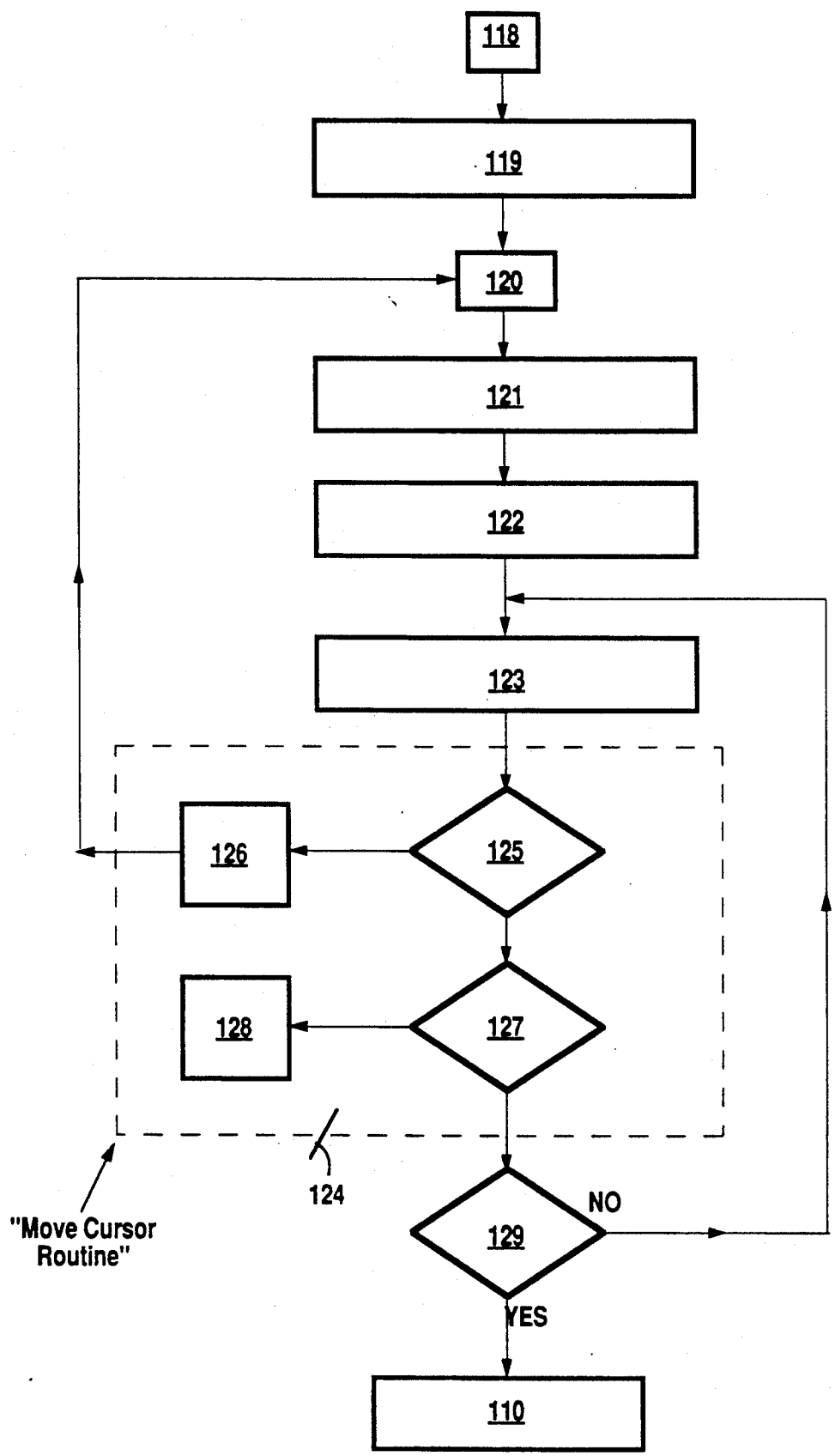
Figure 9C:
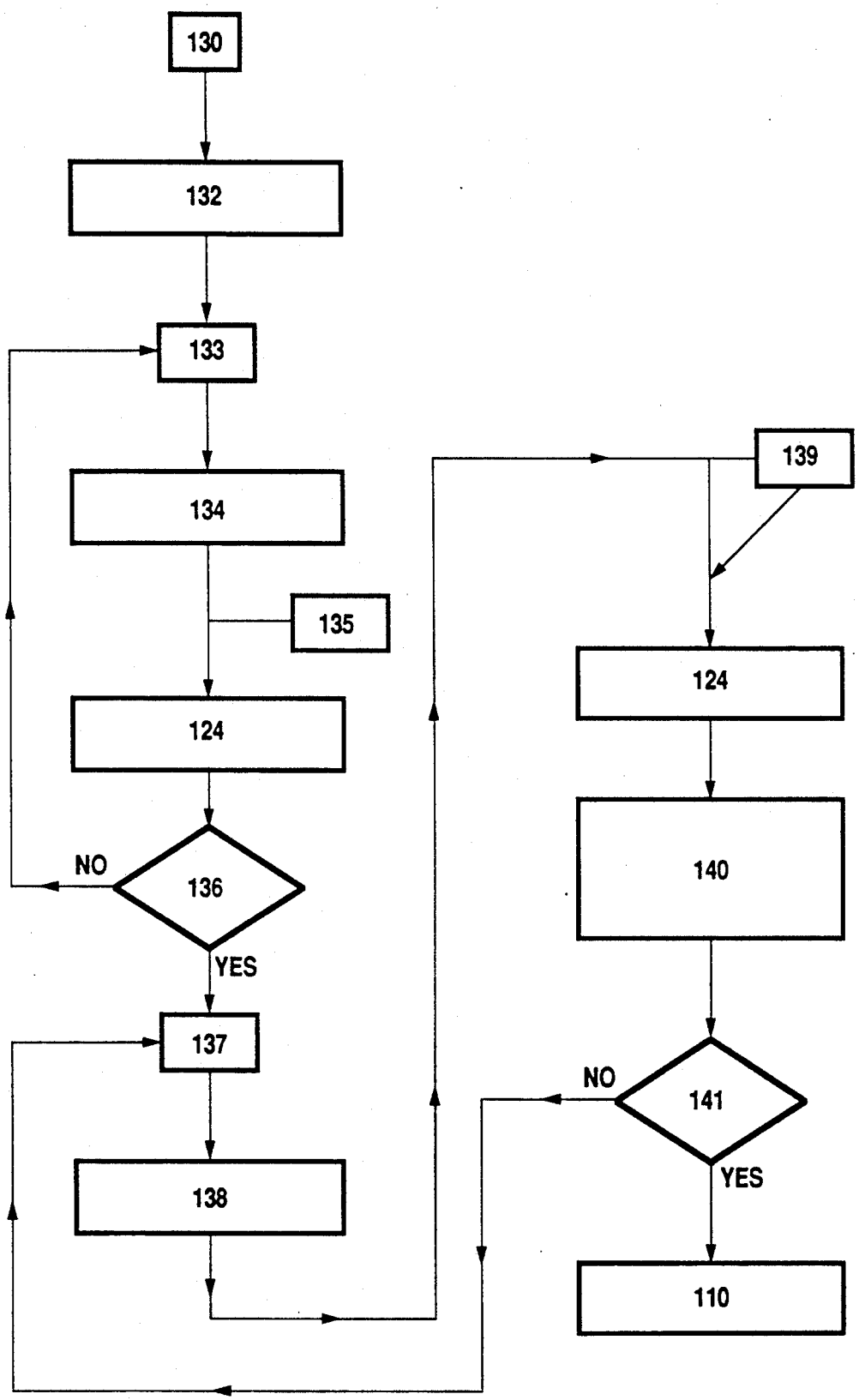

FIG. 9-c depicts a flow chart for a subroutine that allows measurement of responses (8) of the subject while acquiring information about the pupil diameter relative to the baseline (130). Next, by way of a, e.g., "move cursor routine", similar to that illustrated in FIG. 9b, the program allows the user to mark two points on the response waveform. This routine begins by displaying (132) the subject's response (8) to the user. The program displays one cursor on the waveform containing the response (134), and obtains user input (135) to move the cursor (124) to the desired location. Next, the program discerns whether to select the second cursor (136), and if not, returns to step (133) in the subroutine. If so, the program continues on to display the second cursor on the waveform response (138) and to obtain user input (139) for the move cursor routine (124). Finally, the program computes and displays the amplitude and latency differences between the cursors (140). Next, the program discerns whether to quit (141), and if so, returns to the main menu (110). If not, the routine returns to step (137) in the program.

The invention now being fully described, it will be apparent to one of ordinary skill in the art that many changes and modifications can be made thereto without departing from the spirit or scope of the invention as set forth herein.

I claim:

1. An apparatus for evaluating substantially pure phasic-type neuronal activity associated with a specific pattern of pupil diameter variation, comprising
   means for repeatedly measuring pupil diameter and for outputting signals representing the measurements; and
   means operatively connected to the pupil diameter measuring means for evaluating a pattern of pupil diameter variation in response to the presentation to a subject's eye of at least two images capable of eliciting a substantially pure phasic-type neuronal response.

2. The apparatus of claim 1, wherein
   the pupil diameter measuring means comprises a pupillometer.

3. The apparatus of claim 2, wherein
   the pupillometer comprises a pupil image transducer operatively coupled to an electronic scanner for scanning a subject's pupil, and computing means operatively connected to the scanner for determining pupil diameter.

4. The apparatus of claim 3, wherein
the pupil image transducer comprises a video camera.

5. The apparatus of claim 1, wherein the means for evaluating the pattern of pupil diameter variations comprises a data processing system.

6. The apparatus of claim 1, further comprising
visual output means for electronically presenting images of substantially equal luminance to the subject's eye, the visual output means being operatively connected to the means for evaluating the pattern of pupil diameter variation.

7. A method of evaluating substantially pure phasic-type neuronal activity in a subject, comprising
 (1) selecting values for $i_{max}$ about 2 to 100, and for $j_{max}$ of about 4 to 400 and for $k_{max}$ of about 3 to 200;
 (2) blocking the sight of a subject's eye;
 (3) making $i=0$, $j=0$ and $k=o$;
 (4) measuring a subject's pupil diameter;
 (5) making $i=i+1$;
 (6) making $K=k+1$;
 (7) making $j=j+1$;
 (8) providing to the fellow eye an image $I_i$, capable of effecting a substantially pure phasic-type neuronal response in the subject that is associated with a specific pupil diameter variation pattern upon a change in the image;
 (9) measuring the pupil diameter $d_{ij}$ and calculating $v_{ijk} = d_{ijk} - d_{(i=0)jk}$;
 (10) making $j=j+1$;
 (11) repeating steps (7) to (10) every at least about 0.5 sec until $j=j_{max}$;
 (12) repeating steps (6) to (10) every at least about 0.5/sec until $k=k_{max}$;
 (13) repeating steps (5) to (12) until $i=i_{max}$;
 (14) averaging all $v_{ijk}$, wherein $k=o$ to $k_{max}$ to obtain $v^{ave}_{ij}$;
 (15) selecting the highest $v^{ave}_{ij}$, wherein $j=0$ to $j_{max}$, to obtain $v^{ave}_{ih}$; and
 (16) comparing each $v^{ave}_{ih}$ with $v^{ave}_{ih}$ (control) obtained by repeating steps (1) to (15) with at least one control subject lacking any phasic-type abnormal neuronal activity, wherein if the difference between $v^{ave}_{ih}$ and $v^{ave}_{ih}$ (control) is greater than or equal to a predetermined value the phasic-type neuronal activity of the subject is considered abnormal, and if it is equal to or less than the predetermined value it is considered normal.

8. The method of claim 7, wherein
the predetermined value utilized in step (16) is about 2 standard deviations of the $v^{ave}_{ih}$ (control) value.

* * * * *